United States Patent
Chung et al.

(10) Patent No.: US 9,523,672 B2
(45) Date of Patent: Dec. 20, 2016

(54) CELL CULTURE ASSAY

(71) Applicant: Korea University Research and Business Foundation, Seongbuk-gu (KR)

(72) Inventors: Seok Chung, Seoul (KR); Se Woon Han, Gyeonggi-Do (KR); Yoo Jin Shin, Seoul (KR); Jae Young Byun, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/354,423

(22) PCT Filed: Oct. 29, 2012

(86) PCT No.: PCT/KR2012/008917
§ 371 (c)(1),
(2) Date: Apr. 25, 2014

(87) PCT Pub. No.: WO2013/062383
PCT Pub. Date: May 2, 2013

(65) Prior Publication Data
US 2014/0302594 A1  Oct. 9, 2014

(30) Foreign Application Priority Data
Oct. 28, 2011  (KR) .................... 10-2011-0111302

(51) Int. Cl.
*G01N 33/50* (2006.01)
*C12M 3/06* (2006.01)
(Continued)

(52) U.S. Cl.
CPC .......... *G01N 33/5005* (2013.01); *C12M 23/16* (2013.01); *C12M 23/34* (2013.01);
(Continued)

(58) Field of Classification Search
CPC ....... C12M 23/16; C12M 25/14; C12M 41/36; G01N 33/5005
See application file for complete search history.

(56) References Cited

U.S. PATENT DOCUMENTS 6,943,008 B1   9/2005  Ma
2007/0099294 A1   5/2007  Yang et al.

FOREIGN PATENT DOCUMENTS

JP   2002-329511 A   11/2002
JP   2006-71494 A   3/2006
(Continued)

OTHER PUBLICATIONS

Chung et al. "Cell Migration into Scaffolds Under Co-Culture Conditions in a Microfluidic Platform." *Lab Chip.* 9(2009):269-275.
(Continued)

*Primary Examiner* — Nathan Bowers
*Assistant Examiner* — Lydia Edwards
(74) *Attorney, Agent, or Firm* — Mintz Levin Cohn Ferris Glovsky and Popeo, P.C.; Fred C. Hernandez; Linyu L. Mitra (57) ABSTRACT

The present invention relates to a cell culture assay. The present invention comprises: a substrate; a scaffold channel which is formed along the center inside the substrate, and of which at least one is disposed continuously, and inside which a scaffold flows; and a microfluidic channel or channels which is/are respectively formed on one side or on both sides of the scaffold channel, and inside which cells flow, and, here, a leak-preventing part for preventing the scaffold from leaking into the microfluidic channel(s) is formed in at least one of the ceiling surface and the floor surface of a boundary part of the scaffold channel and the microfluidic channel(s).

9 Claims, 8 Drawing Sheets (51) Int. Cl.
- *C12M 1/12* (2006.01)
- *C12M 1/34* (2006.01)
- *C12M 1/00* (2006.01)
- *B01L 3/00* (2006.01)

(52) U.S. Cl.
CPC ............ *C12M 25/14* (2013.01); *C12M 41/36* (2013.01); *C12M 41/46* (2013.01); *B01L 3/502707* (2013.01); *B01L 2200/0647* (2013.01)

(56) References Cited

FOREIGN PATENT DOCUMENTS

| | | |
|---|---|---|
| JP | 2008-519598 A | 6/2008 |
| JP | 2011-516079 A | 5/2011 |
| KR | 20070033685 A | 3/2007 |
| WO | WO-2006/004558 A1 | 1/2006 |
| WO | 2006/052223 A1 | 5/2006 |
| WO | WO-2009/061392 A1 | 5/2009 |
| WO | WO-2009126524 A2 | 10/2009 |
| WO | 2012/050981 A1 | 4/2012 |

OTHER PUBLICATIONS

Jeong et al. "Microfluidic Assay of Endothelial Cell Migration in 3D Interpenetrating Polymer Semi-Network HA-Collagen Hydrogel." *Biomed. Microdevices.* 13(2011):717-723.

Extended European Search Report for Application No. EP 12842801.8, issued Jun. 16, 2015. (7 Pages).

CELL CULTURE ASSAY

CROSS-REFERENCE TO RELATED APPLICATIONS

This application is the U.S. national phase of International Application No. PCT/KR2012/008917 filed Oct. 29, 2012, and claims priority to Korean Patent Application No. 10-2011-0111302 filed Oct. 28, 2011, the disclosures of which are hereby incorporated in their entirety by reference.

BACKGROUND

1. Field of the Invention

The present invention relates to a cell culture assay, and more particularly, to a cell culture assay having a structure which can easily and massively produce cells and more accurately observe a process of culturing cells.

2. Discussion of Related Art

Cell migration means migration of living organisms or individual cells in response of various physical, chemical, and biological stimuli, and is deeply involved with various diseases and biological phenomena in a human body, such as AIDS, pathogenic and bacterial infections, arteriosclerosis, arthritis, periodontitis, psoriasis, cancer, multiple sclerosis, male infertility, asbestos poisoning, ozone poisoning, etc.

However, most conventional cell migration evaluating assays are used for two-dimensional cell migration, and thus could not help observing crawling of cells. Here, since cells actually exist in a three-dimensional space, the conventional assays frequently obtained results different from the real phenomenon.

While assays analyzing three-dimensional cell migration, tissue formation, morphological changes, cell proliferation, etc. have been developed abroad, they had limits to expose cells under specific conditions or simulate real three-dimensional migration occurring in living organisms, and thus did not effectively evaluate and digitize test results.

Here, when scaffolds constituting an extracellular matrix (ECM) are introduced into a microfluidic channel, all advantages of microfluidic technology may be maintained, and reactions of cells in evaluation environments such as cell migration and morphological changes, tissue formation, cell proliferation, etc. can be three-dimensionally simulated.

As a conventional art reflecting such advantages, International Patent No. WO2009/126524 is provided. According to the conventional art, three-dimensional simulation of angiogenesis is succeeded by introducing a collagen scaffold which is one of the ECMs, and results of studies on reactions between vascular endothelial cells and cancer cells, between liver cells and vascular endothelial cells, and between nerve cells.

Here, the microfluidic technology can provide microenvironments around a cell, allow real-time observation and accurate quantification of a reaction of cells, reduce an amount of cells or samples used in a test, and evaluate various test conditions.

In addition, a scaffold-integrating technique can three-dimensionally introduce cells, culture cells in various directions, such as inside and both sides of a scaffold. Therefore, various cells can be cultured at the same time, and thereby interaction of the cells and interaction between the cells and the scaffolds can be studied. For this reason, the scaffold-integrating technique can also be applied in development of medical materials. Moreover, effects of various materials including a nanomaterial, a drug, and a protein on cells may be three-dimensionally evaluated.

However, a microfluidic platform according to a conventional art needs a pole array having a size of several tens to several hundreds of micrometers to fix between scaffold channels. If there is no pole, scaffolds may be leaked into the channels, and therefore the conventional microfluidic platform cannot be applied. With reference, most scaffolds are present in a liquid type. They are solidified after being injected into a specific location in a channel, and therefore a pole is needed to block the injected scaffolds in the specific location before they are solidified.

However, the above-described microfluidic platform has a limit to an area in which cells are reacted due to the pole preventing leakage of the scaffolds, and is very difficult to massively produce cells. In addition, the pole is still seen during observation, which becomes a factor disturbing quantification, and the critical problem is that the cells are preferentially reacted with the pole rather than the scaffolds.

SUMMARY OF THE INVENTION

Technical Problem

Therefore, the present invention is directed to providing a cell culture assay having a structure not allowing cells to be preferentially reacted with scaffolds, and enabling to be fixed between scaffold channels at the same time.

However, the technical object of the present invention to be achieved is not limited to the above-described object, and other objects not described herein will be clearly understood by those of ordinary skill in the art with reference to the following descriptions.

Technical Solution

One aspect of the present invention provides a cell culture assay, which includes a substrate; a scaffold channel which is formed along the center inside the substrate, at least one of which is formed continuously, and inside which a scaffold flows; and a microfluidic channel which is formed on one side or on both sides of the scaffold channel, and inside which cells flow. At least one of the ceiling surface and the floor surface of a boundary part of the microfluidic channel and the scaffold channel includes a leak-preventing part for preventing the scaffold from leaking into the microfluidic channel.

The microfluidic channel and the scaffold channel have semicircular upper parts, and the semicircular upper parts are in contact with each other so that the leak-preventing part is formed at the boundary part therebetween.

The leak-preventing part has a cross section which has a sharp tip and both sides of which are curved.

The leak-preventing part is formed to have a rounded tip.

The leak-preventing part is formed to have a tip having a square cross section.

The leak-preventing part is formed to account for 5% to 95% of the height of the scaffold channel and the microfluidic channel.

The scaffold channel and the microfluidic channel are alternately and repeatedly disposed.

Both ends of the microfluidic channel extend in a direction being distant from the scaffold channel.

Effect of the Invention

According to the present invention, as a leak-preventing part extends to a ceiling surface or a floor surface of a boundary part of a scaffold channel and a microfluidic channel, cells are prevented from reacting first with other structures, thereby enabling accurate quantification in observation of cell culture and a reaction of cells and interaction of cells to be studied.

In addition, as a scaffold channel and a microfluidic channel are disposed in various manners, a test time may be reduced by simultaneously observing various cells.

DETAILED DESCRIPTION OF EXEMPLARY EMBODIMENTS

Hereinafter, an embodiment of a cell culture assay of the present invention will be described in detail with reference to the accompanying drawings.

Figure 1:
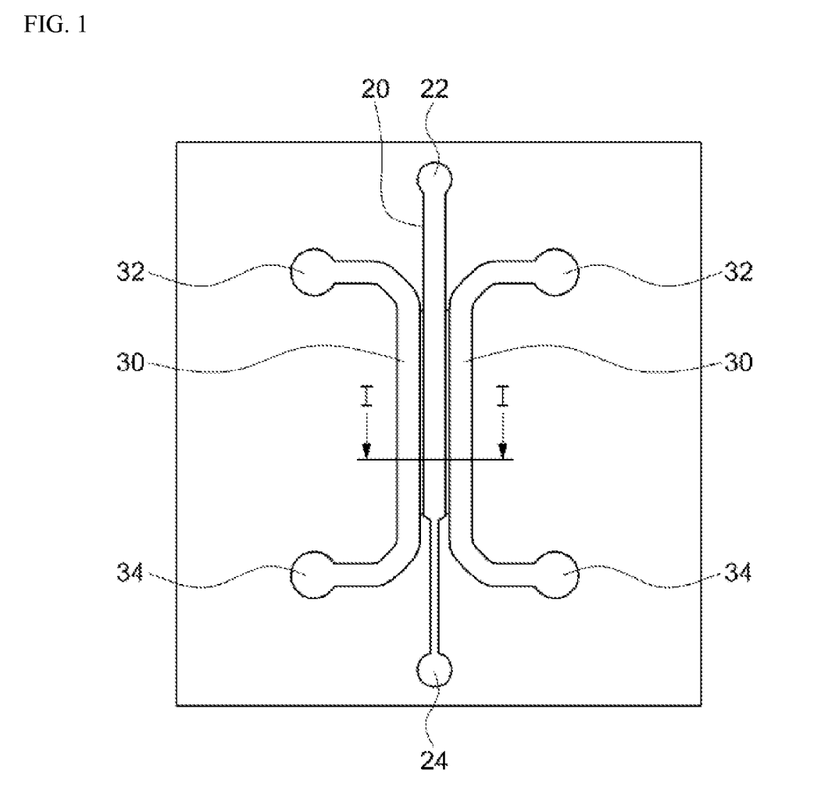
FIG. 1 is a plan view of a cell culture assay according to one embodiment of the present invention.
Figure 2:
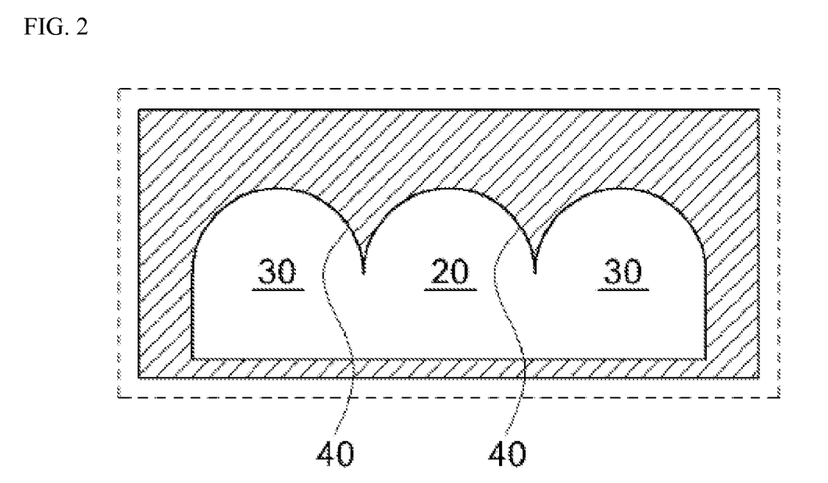
FIG. 2 is a cross-sectional diagram taken along line I-I of FIG. 1.

FIG. 1 is a plan view of a cell culture assay according to one embodiment of the present invention, and FIG. 2 is a cross-sectional view taken along line I-I of FIG. 1.

As shown in FIG. 1, a scaffold channel 20 and a microfluidic channel 30 are each formed on a rectangular substrate 10. The substrate 10 may be formed of a material that can realize a microfluidic structure in which a very small amount of any material can be transferred.

The microfluidic channels 30 in which cells flow are disposed at both sides of the substrate 10, and the scaffold channel 20 is disposed between the microfluidic channels 30. Although will be described below, a plurality of scaffold channels 20 may be sequentially disposed between the microfluidic channels 30.

The scaffold channels 20 are disposed in a straight line across the center of the substrate 10. A scaffold inlet 22 is formed in a front end (upstream) of the scaffold channel 20, and a scaffold outlet 24 is formed in a rear end (downstream) thereof. In addition, microfluid inlet and outlet 32 and 34 are respectively formed in front and rear ends of the microfluidic channel 30.

In the embodiment, in the scaffold channel 20, scaffolds 50 (refer to FIG. 3a) flow, and due to the scaffolds 50 constituting an extracellular matrix (ECM), all of advantages of the microfluidic technology are maintained and a three-dimensional reaction of cells in evaluation of the cell flow may be simulated. Such scaffolds 50 must flow inside the scaffold channel 20 and must not leak into the microfluidic channel 30. In addition, the scaffolds 50 are a liquid type, and thus are solidified after being injected into a specific location in the scaffold channel 20.

In the embodiment, the scaffolds 50 may be formed of a material which becomes solidified or gelated, cured, sticky, or is formed into a pipe form, after being injected in a fluid type. To solidify the scaffolds 50, a method of applying heat, chemically mixing, taking predetermined time, or irradiating light (particularly, UV rays) may be used. In addition, the solidified or gelated scaffolds 50 may be formed of alginate, collagen, a peptide, fibrin, hyaluronic acid, agarose, or PEG, and alternatively, a hydrogel, a general gel, an agarose gel, a tissue, a protein, or an actual matrix material may be used. In addition, the scaffolds 50 may be formed of a material directly extracted from a living body, for example, cells, a cell cluster, or living tissues, or a mixture thereof.

Here, as in the conventional art, when the scaffolds 50 are blocked in a specific location by a pole array, cells are preferentially reacted with the pole array rather than the scaffolds 50, a problem of which may be solved, in the embodiment, by disposing a leak-preventing part 40 at a boundary part in which the scaffold channel 20 meets the microfluidic channel 30. That is, the conventional pole array is removed, and the leak-preventing part 40 is formed to extend to a predetermined length on a ceiling surface or floor surface in the boundary part of the scaffold channel 20 and the microfluidic channel 30.

Figure 3A:
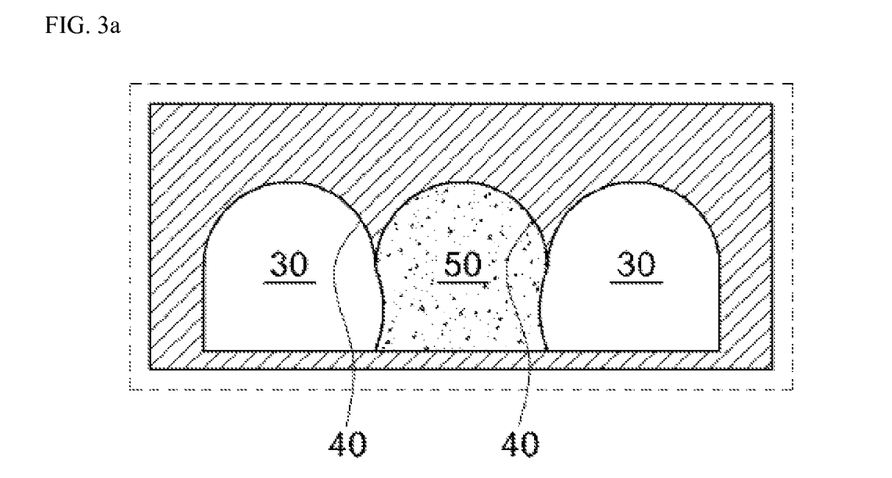
FIGS. 3A and 3B are diagrams showing that a scaffold is injected into the cell culture assay according to one embodiment of the present invention and then solidified.
Figure 3B:
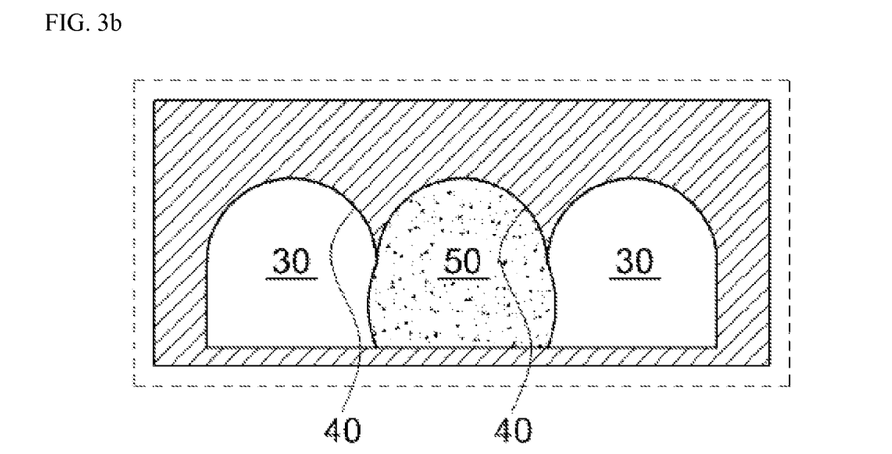

As described above, the process of injecting the scaffolds 50 while the leak-preventing part 40 is formed is simply shown in FIGS. 3A and 3B. Referring to FIGS. 3A and 3B, when the scaffolds 50 first flow into the scaffold channel 20, as shown in FIG. 3A, due to cohesive strength of the scaffolds 50 by themselves, both ends of the scaffold channel may have an inwardly depressed shape, and as time passes, the scaffolds 50 are scattered to both sides, as shown in FIG. 3B, they have a protruding shape. The shape may depend on a surface contact angle of the channel, and may be manipulated in a specific shape. According to the above-described process, the scaffolds 50 may be prevented from leaking into the microfluidic channel 30 due to surface tension with the leak-preventing part 40.

Meanwhile, the leak-preventing part 40, as described above, may be formed on a ceiling surface or floor surface of the boundary part of the scaffold channel 20 and the microfluidic channel 30, and in FIG. 2, it is shown that the leak-preventing part 40 is formed on the ceiling surface. Most preferably, as shown in FIG. 2, the leak-preventing part 40 has a cross section which has a sharp tip and both sides of which are curved. This shape may be realized by forming upper parts of the scaffold channel 20 and the microfluidic channel 30 in a semicircular shape, and disposing the semicircular parts in contact with each other.

Figure 4:
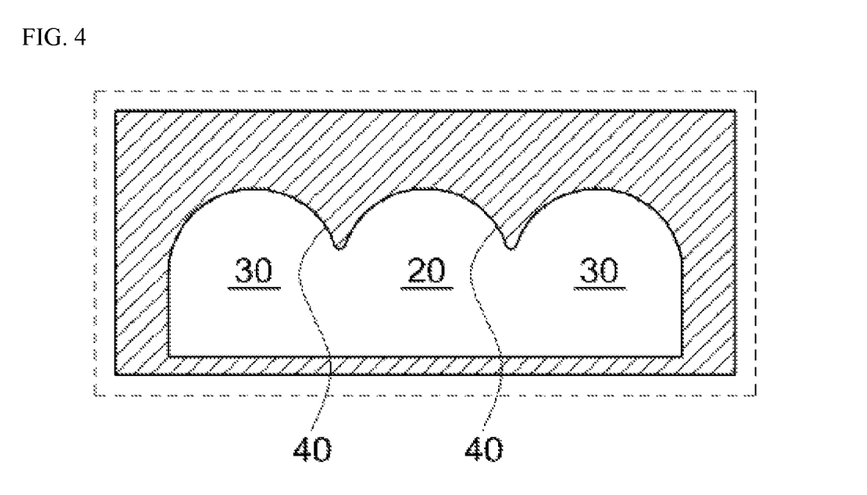
FIGS. 4 and 5 are cross-sectional views of different shapes of channels of the cell culture assay of the present invention.
Figure 5:
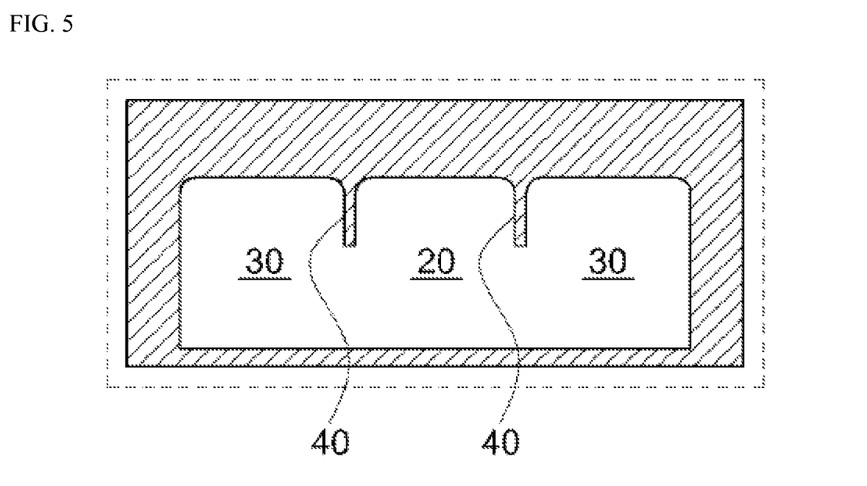

However, in the process of forming the substrate 10 in practice, instead of the sharp tip formed as shown in FIG. 2, a rounded tip may be formed as shown in FIG. 4. In addition, as shown in FIG. 5, the leak-preventing part 40 may be formed to have a square cross section.

As a result, the above-described leak-preventing part 40 extends to a predetermined length on the ceiling surface or the floor surface of the boundary part of the scaffold channel 20 and the microfluidic channel 30, but a shape of the leak-preventing part 40 is not particularly limited.

In addition, the leak-preventing part 40 may be formed to account for 5% to 95% of the height of the scaffold channel 20 and the microfluidic channel 30. Here, when the leak-preventing part 40 is formed to account for less than 5% of the height of the scaffold channel 20 and the microfluidic channel 30, capillarity may be difficult to be maintained, and when the leak-preventing part 40 is formed to account for more than 95%, a drug/molecule may not be actively migrated. For example, the leak-preventing part 40 may be formed to account for various ranges, for example, 20% to 80%, 30% to 70%, or 40% to 60% of the height of the scaffold channel 20 and the microfluidic channel 30.

Meanwhile, both ends of the microfluidic channel 30 extend in a direction being distant from the scaffold channel 20 or in various methods. Accordingly, the scaffolds 50 substantially meet the fluid between the upstream and the downstream. In addition, cells may be cultured in various directions such as inside and both sides of the scaffold channel 20, and various cells can be cultured at the same time. In addition, using the above-described structure, interaction between cells and interaction between cells and scaffolds can be studied, which can be applied in development of medical materials.

Figure 6A:
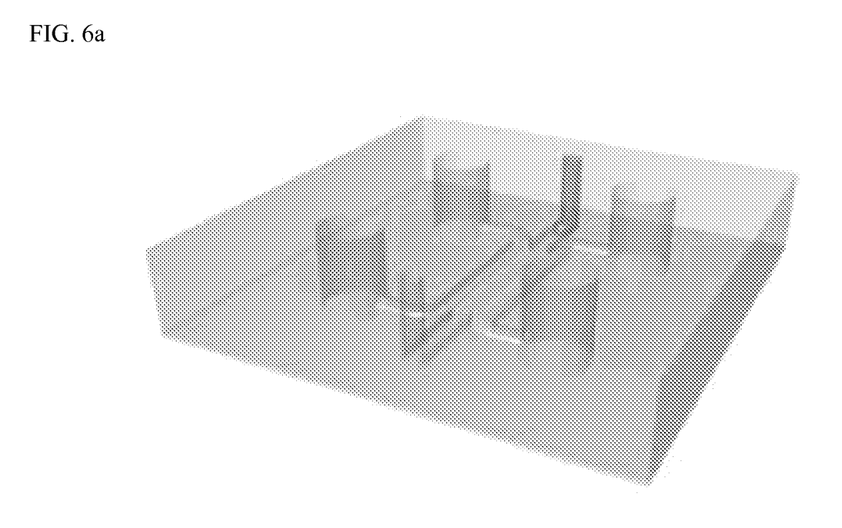
FIGS. 6A to 6C are perspective views showing a process of injecting a scaffold into the cell culture assay according to one embodiment of the present invention.
Figure 6B:
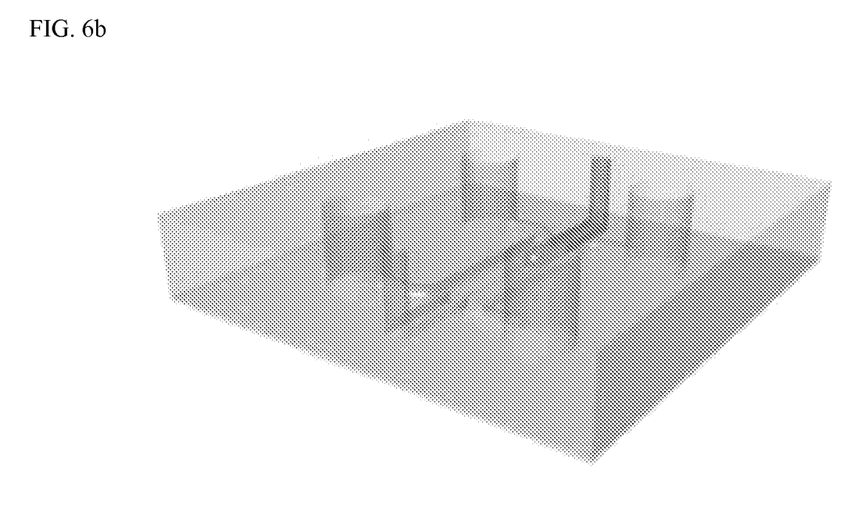
Figure 6C:
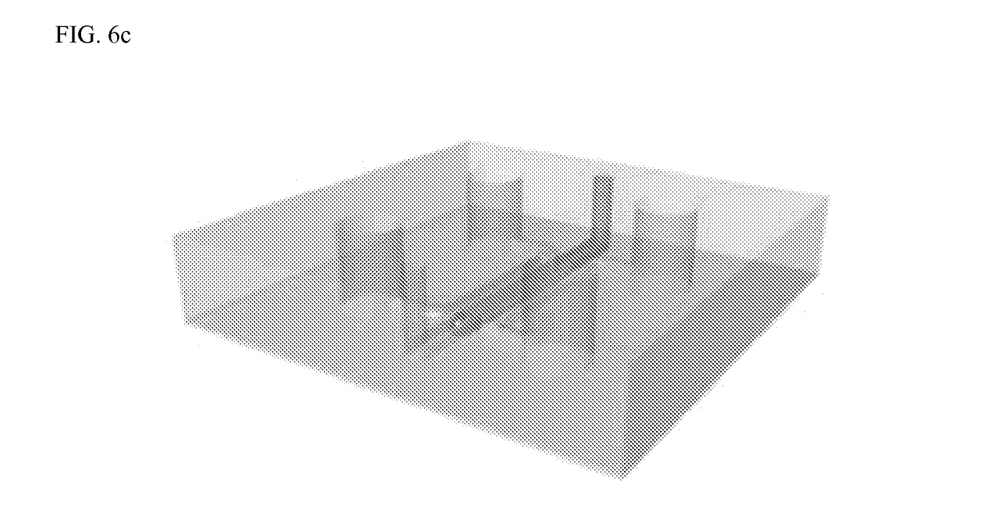

Meanwhile, FIGS. 6A to 6C are perspective views showing a process of injecting scaffolds to the cell culture assay according to one embodiment of the present invention.

As shown in FIGS. 6A to 6C, the scaffolds 50 are injected into the scaffold inlet 22, and flow along the scaffold channel 20. In addition, the scaffold 50 may be fixed on the scaffold channel 20 without leaking into the microfluidic channel 30 due to the leak-preventing part 40 although injected in an amount indicated in FIG. 6C.

Figure 7A:
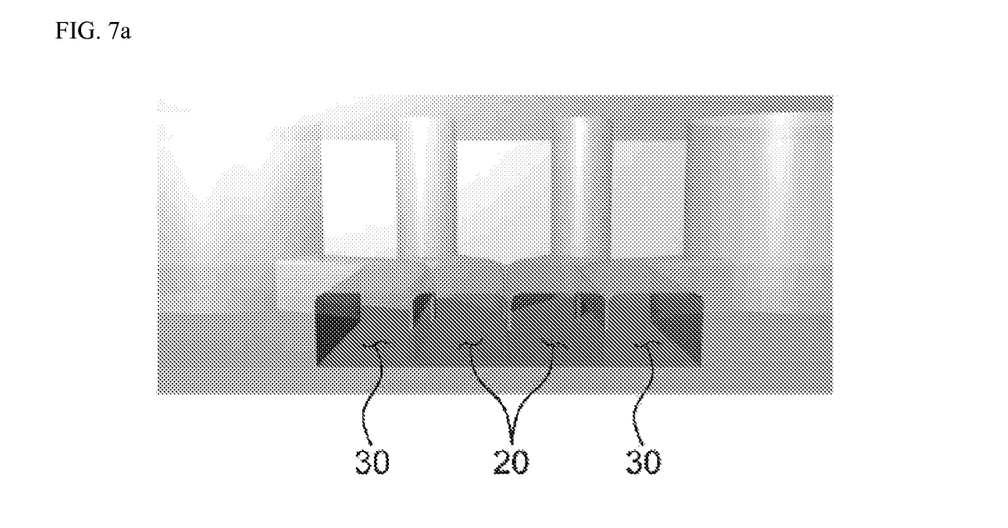
FIGS. 7A and 7B are perspective views showing cross sections of different channel structures of the cell culture assay of the present invention.
Figure 7B:
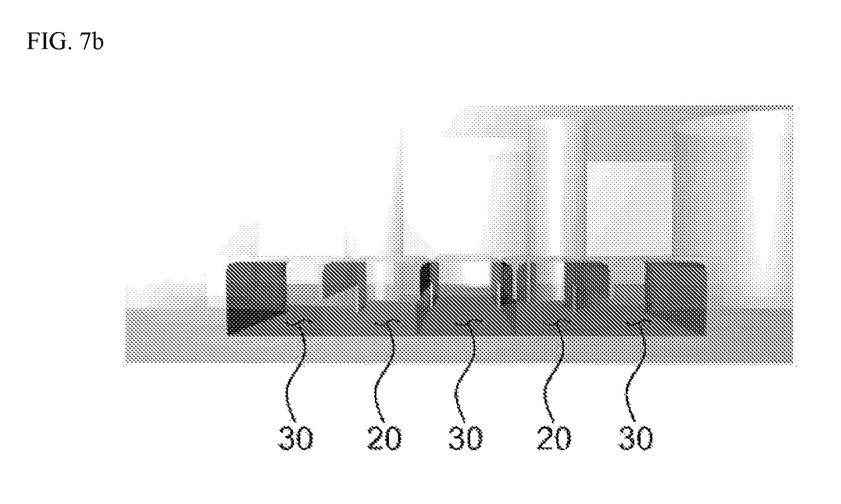

Then, FIGS. 7A and 7B are perspective views of cross sections of different channel structures of the cell culture assay according to the present invention.

As shown in FIGS. 7A and 7B, the scaffold channel 20 and the microfluidic channel 30 of the cell culture assay may be disposed in various manners. In the above-described embodiment with reference to FIG. 2, the microfluidic channels 30 are disposed at both sides, and one scaffold channel 20 is disposed therebetween.

However, arrangement of the scaffold channel 20 and the microfluidic channel 30 is not necessarily limited to the above-described embodiment, as shown in FIG. 4, a plurality of scaffold channels 20 may be sequentially disposed, and as shown in FIG. 5, the scaffold channel 20 and the microfluidic channel 30 may be alternately and repeatedly disposed. As the scaffold channel 20 and the microfluidic channel 30 are disposed in various ways as described above, various kinds of cell culture may be simultaneously confirmed.

Hereinafter, embodiments of cell culture according to the conventional art and the present invention will be compared by images with reference to FIGS. 8 and 9.

Figure 8:
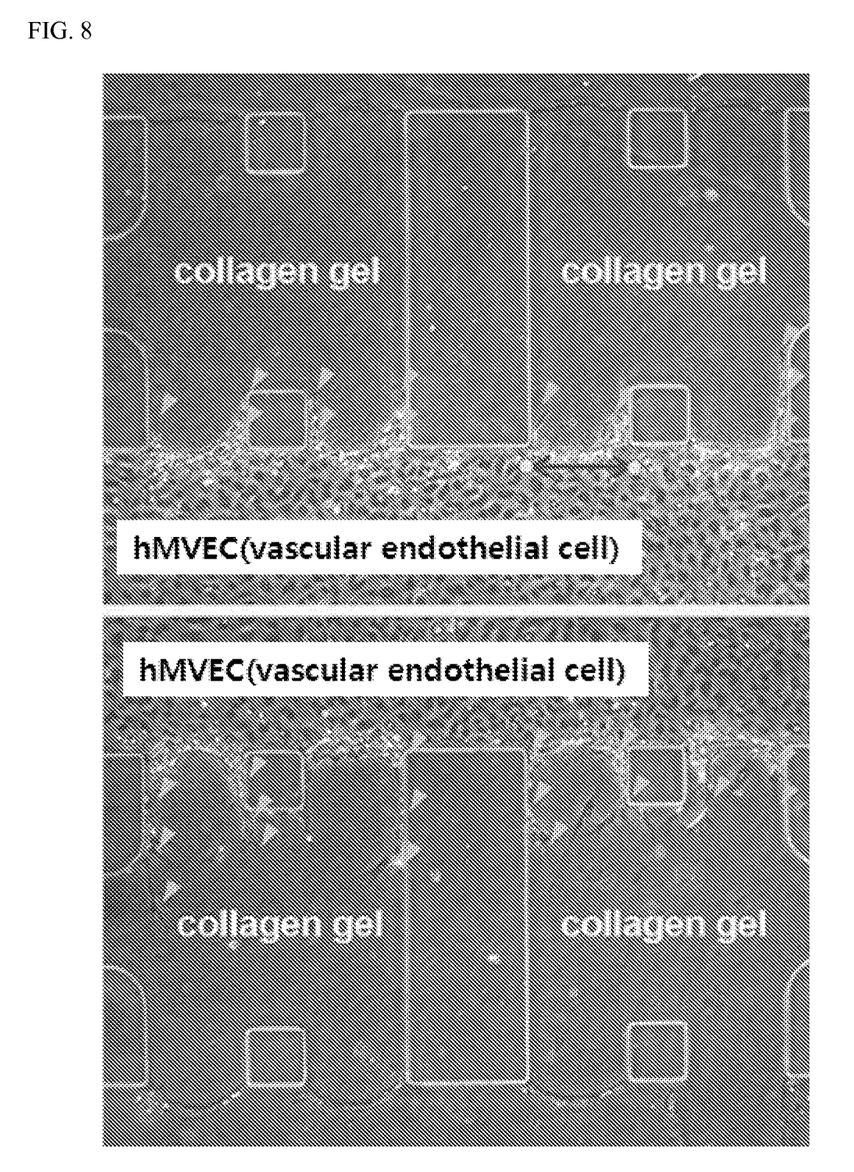
FIG. 8 is an image showing a cell culturing state in a conventional cell culture assay.

FIG. 8 shows culture of vascular endothelial cells through the conventional cell culture assay. Referring to FIG. 8, it could be confirmed that, according to a part represented in yellow, vascular endothelial cells are grown along a pole array and a wall in the conventional art. That is, there is a limit to an area in which the cells are reacted, the pole is still shown during observation, which disrupts quantification, and the cells are preferentially reacted with the pole array. In addition, parts represented in red are preferably wider to observe interactions between cells, between cells and gels, and by chemical factors. However, to maintain surface tension, the parts in red have a limit to be enlarged.

Figure 9:
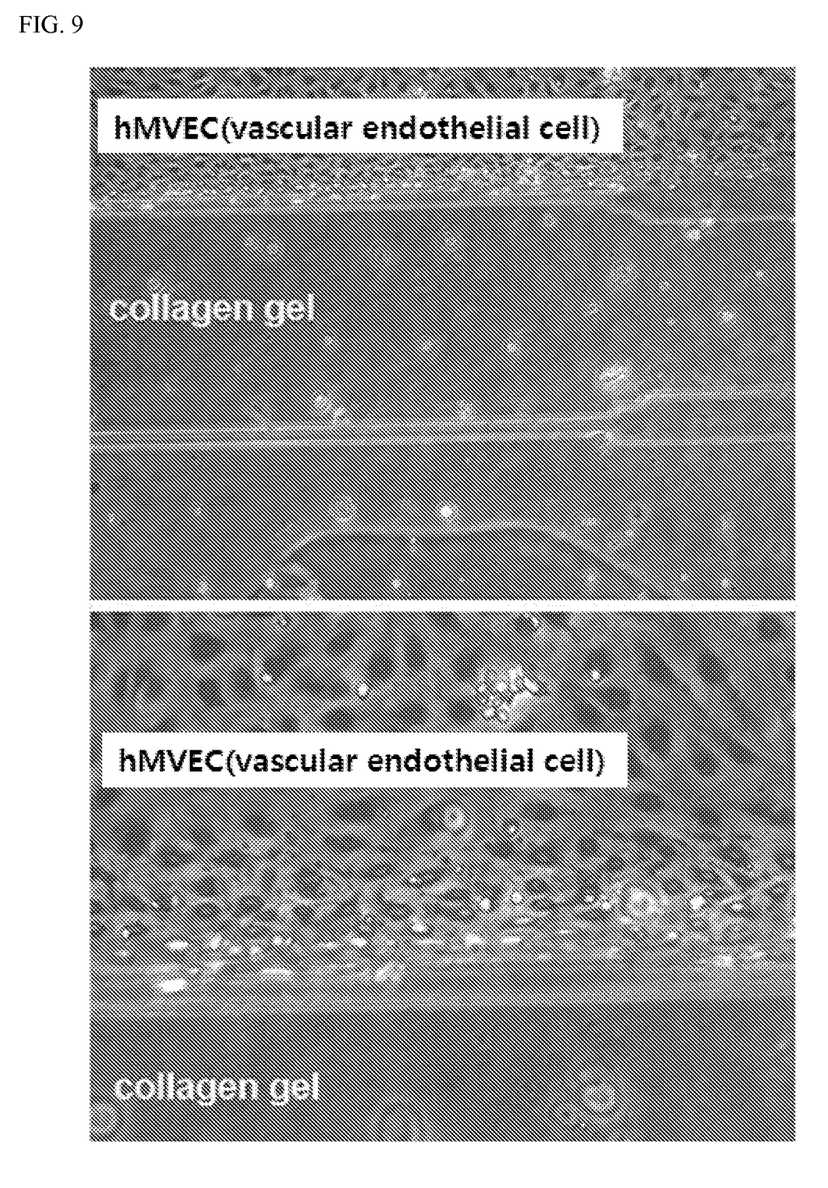
FIG. 9 is an image showing a cell culturing state in the cell culture assay of the present invention.

On the other hand, referring to FIG. 9, it can be confirmed that the vascular endothelial cells are stably grown. Therefore, according to the cell culture assay of the present invention, the interactions between cells, between cells and gels and by chemical factors are easily observed, and the substrate is also easily formed.

In addition, referring to FIGS. 8 and 9, the vascular endothelial cells are used as an example, but it is apparent that the cell culture assay according to the present invention uses various cells including the vascular endothelial cells.

Meanwhile, the cell culture assay described above is generally used in evaluation of cell migration under various environmental conditions, and can be applied in various uses such as development of new drugs, construction of disease models such as cancers, Alzheimer's, etc., construction of tissues and organ models, simulation of biological environment, toxicity evaluation, drug evaluation, contamination evaluation, protein and other material evaluation, biocompatibility evaluation, stem cell studies, etc.

While the invention has been shown and described with reference to certain exemplary embodiments thereof, it will be understood by those skilled in the art that various modifications in form and details may be made therein without departing from the spirit and scope of the invention as defined by the appended claims.

What is claimed is:

1. A cell culture assay, comprising:
   a substrate;
   a scaffold channel which is formed along the centre inside the substrate, and of which at least one is disposed continuously, and inside which a scaffold flows; and
   a microfluidic channel which is formed on one side or on both sides of the scaffold channel, and inside which cells flow, wherein at least one of the ceiling surface and the floor surface of a boundary part of the microfluidic channel and the scaffold channel includes a leak-preventing part for preventing the scaffold from leaking into the microfluidic channel, and
   wherein the leak-preventing part is formed to account for 20% to 80% of the height of the scaffold channel and the microfluidic channel,
   wherein the leak-preventing part is continuously disposed at a boundary part in which the scaffold channel meets the microfluidic channel in a longitudinal direction,
   wherein the cell culture assay does not comprise a pole array to fix between scaffold channels.

2. The cell culture assay of claim 1, wherein the microfluidic channel and the scaffold channel have semicircular upper parts, and the semicircular upper parts are in contact with each other, so that the leak-preventing part is formed at the boundary part therebetween.

3. The cell culture assay of claim 1, wherein the leak-preventing part has a sharp tip having a cross section, the both sides of which are in the shape of a curve.

4. The cell culture assay of claim 1, wherein the leak-preventing part is formed to have a rounded tip.

5. The cell culture assay of claim 1, wherein the leak-preventing part is formed to have a tip having a square cross section.

6. The cell culture assay of claim 1, wherein the scaffold channel and the microfluidic channel are disposed in an alternate and repetitive manner.

7. The cell culture assay of claim 1, wherein the microfluidic channel has both ends extending in a direction being distant from the scaffold channel.

8. The cell culture assay of claim 1, wherein the scaffold is injected in a fluid form to gelate or is formed of curable materials.

9. The cell culture assay of claim 1, wherein the scaffold is formed of one of alginate, collagen, peptide, fibrin, hyaluronic acid, agarose, polyhydroxyethylmethacrylate (PHEMA), polyvinyl alcohol (PVA), Poly(ethylene glycol) (PEG), Poly(ethylene oxide)(PEO), polyethylene (glycol)

diacrylate (PEGDA), gelatin, matrigel, poly(L-lactic acid) (PLLA), carboxymethylcellulose, SAP, PHEMA-MMA, dextran, and chitosan or a mixture of two or more materials.

\* \* \* \* \*